United States Patent [19]

Schaffer

[11] Patent Number: 5,817,913
[45] Date of Patent: Oct. 6, 1998

[54] METHOD FOR BREEDING TOMATOES WITH SUPERIOR TASTE CHARACTERISTICS AND PRODUCT OF THE METHOD

[75] Inventor: Arthur Schaffer, Hashmonaim, Israel

[73] Assignee: Peri Devlopment Applications, Ltd., Bet Dagan, Israel

[21] Appl. No.: 530,216

[22] PCT Filed: Mar. 30, 1994

[86] PCT No.: PCT/US94/03522

§ 371 Date: Nov. 30, 1995

§ 102(e) Date: Nov. 30, 1995

[87] PCT Pub. No.: WO94/22289

PCT Pub. Date: Oct. 13, 1994

[30] Foreign Application Priority Data

Mar. 31, 1993 [IL] Israel ......................................... 105243

[51] Int. Cl.[6] ............................... A01H 5/00; A01H 1/04; A01H 5/08; C12N 5/14; C12P 19/12
[52] U.S. Cl. ......................... 800/200; 800/220; 800/255; 800/DIG. 44; 435/100; 435/172.2; 435/421; 435/423; 47/58; 47/DIG. 1
[58] Field of Search .................................. 47/58, DIG. 1; 435/172.2, 240.45, 100, 421, 423; 800/200, 255, DIG. 44, 220

[56] References Cited

U.S. PATENT DOCUMENTS 4,834,186  5/1989  Nahum ......................................... 800/1
4,940,839  7/1990  Bravo et al. ............................. 800/220

OTHER PUBLICATIONS

Stommel et al. J. Amer. Soc. Hart. Sci. 118(6):859–863, 1993.
Rick, C.M. TGC Report No. 27, p. 21, 1977.
Chetelat et al. The Plant Journal 4(4):643–650, 1993.
Moskowitz, H.R., Ratio scales of sugar sweetness, *Perception & Psychophysics*, 1970, V. 7, No. 5, pp. 315–320.
Stevens, M.A., Inheritance of Tomato Fruit Quality Components, *Plant Breeding Reviews*, V. 4, pp. 273–311.
Davies, J.N., et al., The Constituents of Tomato Fruit—The Influence of Environment, Nutrition, and Genotype, *CRC Critical Reviews in Food Science and Nutrition*, 1981, V. 15, No. 3, pp. 205–280.
Yelle, S., et al., Sink Metabolism in Tomato Fruit, *Plant Physiol.*, 1988, V. 87, pp. 737–740.
Davies, J.N., et al., Changes in the Individual Sugars of Tomato Fruit During Ripening, *J. Sci. Fd Agric.*, 1975, V. 26, pp. 1103–1110.
Azanza et al. Theor. Appl. Genet. 87:965–972, 1994.
Young et al. J. Amer. Soc. Hort. Sci. 118(2):286–292, 1993.
Meyer, A.C., et al. "Estimating Heritability and the Number . . . " Hortscience, vol. 23, No. 3, issued Jun. 1988, pp. 767, abstract No. 346.
Davies, J.N. "Occurence of Sucrose . . . " Nature, vol. 209, issued 5 Feb. 1966, pp. 640–641.
Miron, D., et al. "Sucrose Phosphate Synthase, . . . " Plant Physiology, vol. 95, No. 2, issued Feb. 1991, pp. 623–627.
Yelle, S., et al. "Sink Metabolism in Tomato Fruit . . . " Plant Physiology, vol. 95, No. 4, issued Apr. 1991, pp. 1026–1035.

*Primary Examiner*—David T. Fox
*Attorney, Agent, or Firm*—Ladas & Parry

[57] ABSTRACT

A method for breeding tomato plants that produce tomatoes having superior taste characteristics including the steps, of crossing at least one *Lycopersicon esculentum* plant with a green-fruited *Lycopersicon* spp. from an Eriopersicon subgenus to produce hybrid seeds, collecting the hybrid ($F_1$) seeds, growing plants from $F_1$ seeds, pollinating the $F_1$ plants, collecting the hybrid seeds produced by the $F_1$ plants, growing plants from the seeds produced by the $F_1$ plants, measuring sucrose, glucose and fructose content of ripe fruit produced from the plants grown from the seeds of the $F_1$ plants; and selecting plants with tomato fruits having desired characteristics including a fructose/glucose ratio greater than 1.8 and fructose levels higher than 1.3% on a fresh weight basis.

17 Claims, No Drawings

METHOD FOR BREEDING TOMATOES WITH SUPERIOR TASTE CHARACTERISTICS AND PRODUCT OF THE METHOD

The present invention relates to a method of breeding tomatoes having superior taste characteristics and to tomatoes having superior taste characteristics and to products of the method.

BACKGROUND OF THE INVENTION

Taste characteristics are a major determinant of fruit quality for both processing and fresh market tomatoes (Stevens, M. A., 1986, *Inheritance of Tomato Fruit Quality Components,* Plant Breeding Reviews, 4, 274–310). One of the major components of taste in tomatoes is soluble sugar content.

The soluble sugar content of all known commercial cultivars of tomato (*Lycopersicon esculentum* Mill.) primarily includes the hexose sugars glucose and fructose in ratios of approximately 1:1 to 1:1.5 (Davies, J. N. and Hobson, G. E., 1981, *The Constituents of Tomato Fruit—The Influence of the Environment, Nutrition and Genotype,* CRC Critical Reviews in Food Science and Nutrition, 15: 205–280; Davies, J. N. and Kempton, R. J., 1975, *Chances in the Individual Sugars of Tomato Fruit During Ripening,* J. Sci. Fd. Agric., 26: 1103–1110).

In commercial *L esculentum* cultivars the disaccharide sucrose is also present, but at concentrations rarely exceeding 0.5% on a fresh weight basis. Certain wild species of *Lycopersicon* such as *L. hirsutum* and *L. chmielewskii,* accumulate high concentrations of sucrose, which may reach 4% on a fresh weight basis (Miron, D. and Schaffer A. A., 1991, *Sucrose Phosphate Synthase, Sucrose Synthase and Invertase Activities in Developing Fruit of Lycopersicon esculentum and the Sucrose Accumulating Lycopersicon hirsutum,* Plant Physiol. 95: 623–627 and Yelle S. et al., 1988, *Sink Metabolism in Tomato Fruit. III. Analysis of Carbohydrate Assimilation in Wild Species,* Plant Physiol. 87:737–740). Some of these species, in addition, have a fructose to glucose ratio of more than 1.5; however, fructose and glucose levels in the fruit of these species is very low, below 1.3% each on a fresh weight basis (Davies, J. N. and Kempton, R. J., 1975, *Changes in the Individual Sugars of Tomato Fruit During Ripening,* J. Sci. Fd. Agric., 26: 1103–1110; Davies, J. N., 1966, *Occurrence of Sucrose in the Fruit of Some Species of Lycopersicon,* Nature, 209, 640–641, the disclosure of which is incorporated herein by reference).

Typically, plant breeders seek to increase the sweetness component of tomato flavor by increasing total soluble solids (TSS). TSS is typically estimated by a refractometic determination of a sample of juice and is expressed in °BRIX. The measurement of °BRIX, however, does not differentiate between the component sugars. Selections have recently been made for sucrose accumulating tomatoes (Yelle, S., 1991, *Sink Metabolism in Tomato Fruit IV Genetic and Biochemical Analysis of Sucrose Accumulation,* Plant Physiol. 95, 1026–1035). Fructose, however, is twice as sweet per unit weight as glucose and 50% sweeter than sucrose (Biester, A. M. et al., 1925, *Carbohydrate Studies. I. The Relative Sweetness of Pure Sugars,* Amer. J. Physiol. 73: 387–400) giving a tomato with a high relative fructose content distinct advantages in terms of superior taste characteristics.

SUMMARY OF THE INVENTION

The present invention seeks to provide an improved method for breeding tomato plants having superior taste characteristics and products of the method.

There is thus provided in accordance with the present invention a method for breeding tomato plants that produce tomatoes having superior taste characteristics including the steps of, crossing at least one *Lycopersicon esculentum* plant with a *Lycopersicon* spp. to produce hybrid seeds, collecting the hybrid ($F_1$) seeds, growing plants from the $F_1$ seeds, pollinating the $F_1$ plants, collecting the hybrid seeds produced by the $F_1$ plants, growing plants from the seeds produced by the $F_1$ plants, measuring sucrose, glucose and fructose content of ripe fruit produced from the plants grown from the seeds of the $F_1$ plants; and selecting plants with tomato fruits having desired characteristics including a fructose/glucose ratio greater than 1.8 and fructose levels higher than 1.3% on a fresh weight basis.

In accordance with a preferred embodiment of the present invention the method for breeding tomato plants additionally includes the steps of crossing plants which have been selected according to the method of claim 1 with a *Lycopersicon* plant and selecting plants with tomato fruits having desired characteristics including a fructose/glucose ratio greater than 1.8 and fructose levels higher than 1.3% on a fresh weight basis.

In accordance with a further preferred embodiment of the present invention the steps of crossing and selecting are repeated at least once.

In accordance with yet a further preferred embodiment of the present invention the method for breeding tomato plants additionally includes the steps of selfing, at least once, the plants, and selecting plants with tomato fruits having desired characteristics including a fructose/glucose ratio greater than 1.8 and fructose levels higher than 1.3% on a fresh weight basis.

In accordance with still a further preferred embodiment of the present invention the *Lycopersicon* spp. plant having a fructose: glucose ratio greater than 1.8 is a *Lycopersicon hirsutum* plant.

In accordance with still another preferred embodiment of the present invention crossing includes sexual crossing.

In accordance with yet another preferred embodiment of the invention crossing includes asexual crossing.

In accordance with a further preferred embodiment of the invention asexual crossing includes somatic cell hybridization.

In accordance with a still further preferred embodiment of the invention the step of pollinating includes self pollination.

In accordance with yet a further preferred embodiment of the invention the step of pollination includes back crossing with a *Lycopersicon esculentum* plant.

In accordance with still another preferred embodiment of the present invention the method for breeding tomato plants additionally includes the step of propagating the plants with tomato fruits having the desired characteristics.

In accordance with yet another preferred embodiment of the present invention the step of propagating includes the step of vegetative propagation.

In accordance with a further preferred embodiment of the present invention the step of propagating includes the step of propagation by seed.

In accordance with a still further preferred embodiment of the present invention there is provided a tomato plant produced according to the method described hereinabove.

In accordance with yet a further preferred embodiment of the present invention there is provided a tomato fruit produced by a tomato plant produced according to the method described hereinabove.

In accordance with another preferred embodiment of the present invention there is provided tomato seeds which when grown yield a tomato plant produced according to the method described hereinabove.

There is also provided in accordance with the present invention a heterozygous tomato plant producing fruit having a fructose/glucose ratio greater than 1.8 and fructose levels higher than 1.3% on a fresh weight basis.

In accordance with a preferred embodiment of the present invention the tomato plant includes tomato fruit.

In accordance with a further preferred embodiment of the present invention the tomato plant includes tomato seeds which when grown yield the tomato plant described hereinabove.

DESCRIPTION OF THE PREFERRED EMBODIMENTS

Reference is now made to a method for breeding tomato plants that produce tomatoes having superior taste characteristics including fructose levels, i.e. greater than 1.3% on a fresh weight basis and a fructose/glucose ratio higher than 1.8. The elevated fructose/glucose ratio providing a sweeter taste than that found in tomatoes having a similar amount of total sugars but with a normal fructose to glucose ratio.

The method for breeding tomato plants includes first hybridizing at least one *Lycopersicon esculentum* plant with a *Lycopersicon hirsutum* plant. The fruits of the *L esculentum* plants are then allowed to ripen and the hybrid ($F_1$) seeds are collected.

The collected $F_1$ seeds are then planted. $F_1$ plants are grown and then allowed to self pollinate. The self pollinated flowers are then allowed to produce ripe fruits and the $F_2$ seeds are collected. These seeds are then planted. Plants grown from these seeds are allowed to produce fruits which are harvested.

The harvested fruits are then analyzed for °BRIX, sucrose, glucose and fructose content, using methods described below, and plants with tomato fruits having desired characteristics including a fructose/glucose ratio greater than 1.8 and fructose levels higher than 1.3% on a fresh weight basis are selected.

The selected plants may then be propagated for use by vegetative propagation methods such as micropropagation or by sexual propagation methods. The selected plants may also be selfed for at least one generation or crossed with other i L esculentumcultivars to create varieties which incorporate characteristics other than the high fructose/glucose ratios selected for.

These derived plants may then be propagated either vegetatively or by seed based propagation.

Reference is now be made to the following example which illustrates the invention.

EXAMPLE 1
HYBRIDIZATION

Ten plants of the *L esculentum* breeding line 1630 (a Volcani Institute male sterile breeding line) were crossed with the wild species *L. hirsutum* (LA 1777) using the *L. esculentum* breeding line as the female parent. The *L. esculentum* parent contained approximately equimolar concentrations of glucose and fructose (see Table 1). The *L. hirsutum* parent (LA 1777) accumulated sucrose but had a low concentration of fructose/glucose and a fructose glucose ratio of 2.3 but with less than 1.3% fructose on a fresh weight basis (see Table 1).

The fruits of the *L esculentum* plants were then allowed to ripen and the hybrid ($F_1$) seeds collected. Hybrid $F_1$ seed was sown and plants grown. The plants were allowed to self pollinate and after the ripening of the fruit $F_2$ seed was collected.

The $F_2$ seeds were sown and about 350 $F_2$ plants were grown and allowed to self pollinate. The fruits were allowed to ripen and fruit from each individual plant which produced fruit was harvested and individually analyzed for TSS (°BRIX), and soluble sugar content, as described hereinbelow.

Only 25 of the interspecific $F_2$ plants freely produced fruit. Seed was collected from all plants. The most promising four plants which showed desired characteristics including a fructose/glucose ratio greater than 1.8 and fructose levels higher than 1.3% on a fresh weight basis were used to produce $F_3$ populations. Again $F_3$ seed was sown and the plants were allowed to self pollinate and produce fruit and ripe fruit of individual plants was analyzed as described hereinbelow.

MEASUREMENT OF °BRIX AND SOLUBLE SUGAR (SUCROSE, GLUCOSE AND FRUCTOSE) OF MATURE FRUIT PERICARP

Individual fruits were harvested. The juice was manually expressed from a portion of the fruit pericarp and a few drops placed on a refractometer and °BRIX values read. An additional portion of the fruit tissue was placed in 80% ethyl alcohol and heated to 70° C. in order to stop enzymatic activity and extract the soluble sugars. Soluble sugars were extracted three times in successive changes of 80% alcohol which was then evaporated.

The sugars were then dissolved in double distilled water, centrifuged at 5,000 rpm in an eppendorf centrifuge tube for 15 min. to remove debris and a 0.5 ml aliquot passed through a 0.45 micron filter in preparation of High Pressure Liquid Chromotography (HPLC) analysis. HPLC analysis was performed using a BioRad (Richmond, Calif., USA) Fast Carbohydrate column for the separation of glucose, fructose and sucrose according to the manufacturers instructions. The sugars were identified and quantified according to the chromatographic behavior of standards for the sugars which were obtained from Sigma (St. Louis, Mo., USA).

The sucrose, glucose and fructose values of fruit of selected $F_3$ plants are shown in Table 1.

TABLE 1

| Percent Gram Fresh Weight of Individual Sugars in Selected Ripe $F_3$ Tomato Fruit | | | | | |
|---|---|---|---|---|---|
| Plant No. | Suc. | Glu. | Fru. | Total Sugars | Fru/Glu ratio |
| Parents | | | | | |
| L. esculentum 1630 | .20 | 1.10 | 1.40 | 2.70 | 1.27 |
| L. hirsutum LA 1777 | 4.90 | .30 | .70 | 5.90 | 2.30 |
| F3 Plants | | | | | |
| 200–01 | .97 | .66 | 3.11 | 4.74 | 4.71 |
| 201–10 | 2.50 | 1.45 | 2.87 | 6.82 | 1.98 |
| 203–07 | .58 | .85 | 3.58 | 5.01 | 4.21 |
| 203–10 | .28 | 1.30 | 3.37 | 4.95 | 2.59 |

It will be appreciated by persons skilled in the art that the present invention is not limited to what has been particularly shown and described hereinabove. Rather the scope of the present invention is defined only by the claims which follow:

I claim:

1. A method for breeding tomato plants that produce tomatoes having superior taste characteristics comprising the steps of:
    crossing at least one *Lycopersicon esculentum* plant with a green-fruited *Lycopersicon* spp. from an Eriopersicon subgenus to produce hybrid seeds;
    collecting the hybrid ($F_1$) seeds;
    growing plants from the $F_1$ seeds;
    pollinating the $F_1$ plants;
    collecting the hybrid seeds produced by the $F_1$ plants;
    growing plants from the seeds produced by the $F_1$ plants;
    measuring sucrose, glucose and fructose content of ripe fruit produced from the plants grown from the seeds of the $F_1$ plants; and
    selecting plants with tomato fruits having desired characteristics including a fructose/glucose ratio greater than 1.8 and fructose levels higher than 1.3% on a fresh weight basis.

2. A method according to claim 1, and additionally comprising the steps of:
    crossing plants which have been selected according to the method of claim 1, with a *Lycopersicon* plant and selecting plants with tomato fruits having desired characteristics including a fructose/glucose ratio greater than 1.8 and fructose levels higher than 1.3% on a fresh weight basis.

3. A method according to claim 2, wherein the steps of crossing and selecting are repeated at least once.

4. A method according to claim 1, wherein crossing includes sexual crossing.

5. A method according to claim 1, wherein crossing includes asexual crossing.

6. A method according to claim 5, wherein asexual crossing includes somatic cell hybridization.

7. A method according to claim 1, wherein the step of pollinating includes self pollination.

8. A method according to claim 1, wherein the step of pollination includes back crossing with a *Lycopersicon esculentum* plant.

9. A method according to claim 1, wherein the *Lycopersicon* spp. plant having a fructose:glucose ratio greater than 1.8 is a *Lycopersicon hirsutum* plant.

10. A method according to claim 1, and additionally comprising the step of propagating the plants with tomato fruits having the desired characteristics.

11. A method according to claim 10, wherein the step of propagating includes the step of vegetative propagation.

12. A method according to claim 10, wherein the step of propagating includes the step of propagation by seed.

13. A tomato plant produced according to the method of claim 1.

14. A tomato fruit produced by a tomato plant in accordance with claim 13.

15. Tomato seeds which when grown yield a tomato plant in accordance with claim 13.

16. A heterozygous tomato plant producing fruit having a fructose/glucose ratio greater than 1.8 and fructose levels higher than 1.3% on a fresh weight basis.

17. Tomato seeds which when grown yield a tomato plant in accordance with claim 16.

* * * * *